Figure 1:
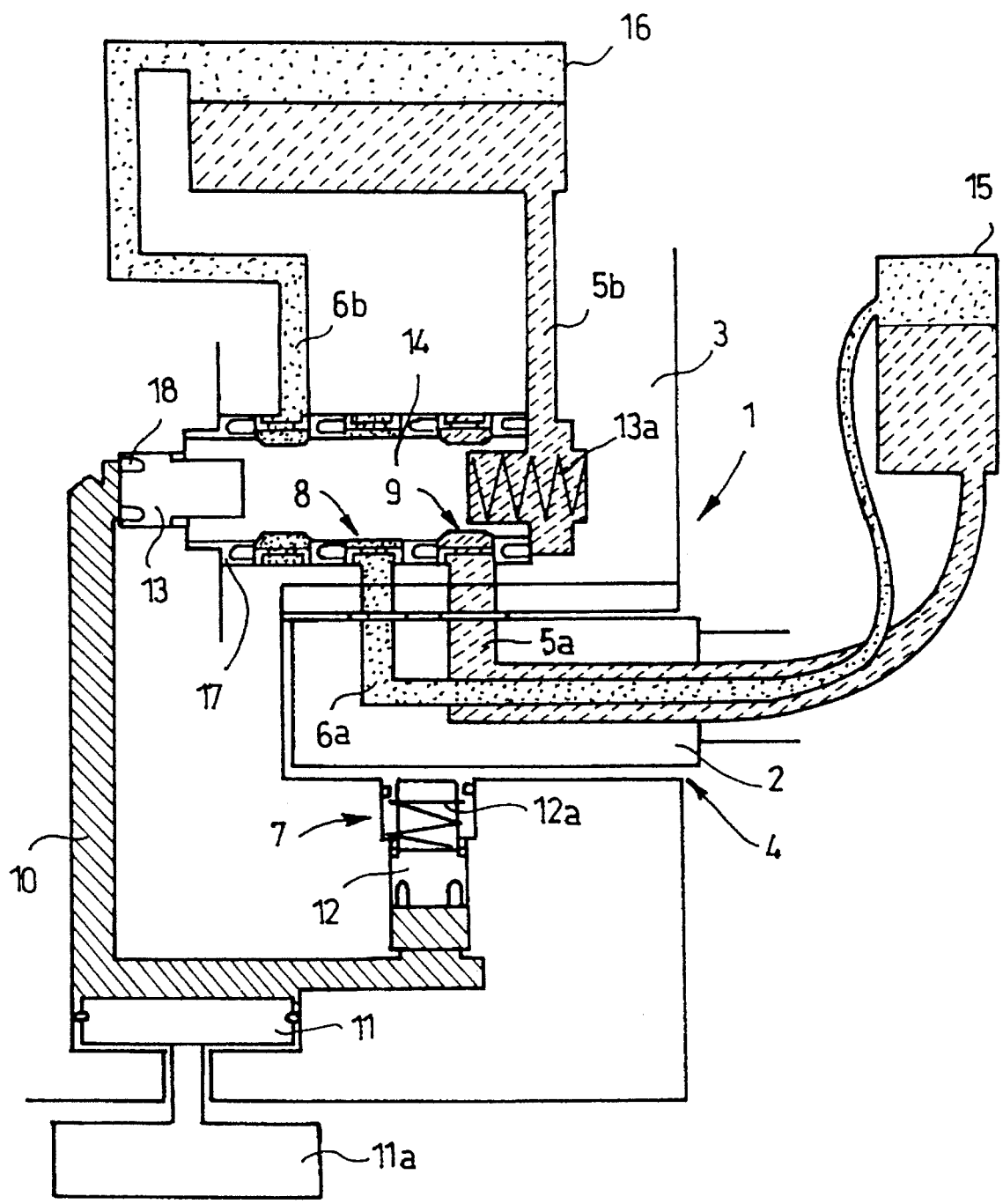

United States Patent [19]

Heinonen et al.

[11] Patent Number: 5,585,045
[45] Date of Patent: Dec. 17, 1996

[54] ARRANGEMENT FOR FILLING AN ANAESTHETIC VAPORISER

[75] Inventors: Erkki Heinonen; Jukka Kankkunen, both of Helsinki, Finland

[73] Assignee: Instrumentarium Oy, Finland

[21] Appl. No.: 522,844

[22] Filed: Sep. 1, 1995

[30] Foreign Application Priority Data

Oct. 18, 1994 [FI] Finland ................. 944888

[51] Int. Cl.⁶ ................................ B01F 3/04
[52] U.S. Cl. .................. 261/72.1; 128/203.26; 128/202.27; 128/203.12
[58] Field of Search ............ 261/72.1, DIG. 65; 128/203.26, 202.27, 203.12

[56] References Cited

U.S. PATENT DOCUMENTS

| | | | |
|---|---|---|---|
| 4,879,997 | 11/1989 | Bickford | 128/203.12 |
| 4,883,049 | 11/1989 | McDonald | 128/203.12 |
| 5,427,145 | 6/1995 | Grabenkort | 128/203.12 |
| 5,478,506 | 12/1995 | Lavimodiere | 261/72.1 |
| 5,505,236 | 4/1996 | Grabenkort et al. | 128/202.27 |

FOREIGN PATENT DOCUMENTS

| | | |
|---|---|---|
| 455433 | 11/1991 | European Pat. Off. . |
| 923196 | 1/1994 | Finland . |
| 4106756 | 9/1992 | Germany . |

*Primary Examiner*—Tim R. Miles
*Attorney, Agent, or Firm*—Andrus, Sceales, Starke & Sawall

[57] ABSTRACT

An arrangement for filling an anaesthetic vaporiser, the arrangement comprising a filling device to be connected to a transport package for an anaesthetic agent, the filling head of the device being attachable to an opening in the vaporiser. The arrangement comprises a fastening means for clamping the filling head against the sealing surface of conduits leading to the opening, and a valve means arranged to open when the filling head is in the clamped position against the sealing surface of the conduits leading to the opening and thus arranged to allow the flow of the anaesthetic agent between the vaporiser and the transport package and the flow of the substitute gas in the opposite direction between the transport package and the vaporiser. In order to provide simple operation, the arrangement further comprises a hydraulic container comprising arranged thereto a first piston means used to control the pressure of the hydraulic container, a second piston means connected to the fastening means, and a third piston means connected to one or several valve means one of which controls the flow of the anaesthetic agent.

17 Claims, 3 Drawing Sheets

ARRANGEMENT FOR FILLING AN ANAESTHETIC VAPORISER

The invention relates to an arrangement for filling an anaesthetic vaporiser, the arrangement comprising a filling device to be connected to a transport package for an anaesthetic agent, the filling head of the device being attachable to an opening in the vaporiser, whereupon the filling device and the vaporiser are provided with conduits for transferring the anaesthetic agent between the transport package and the vaporiser and for transferring the substitute gas in the opposite direction, the arrangement comprising a fastening means for clamping the filling head against the sealing surface of conduits leading to the opening in the vaporiser, and one or several valve means arranged to open when the filling head is in the clamped position against the sealing surface of the conduits leading to the vaporiser opening and thus arranged to allow the flow of the anaesthetic agent between the vaporiser and the transport package and the flow of the substitute gas in the opposite direction compared to the anaesthetic agent between the transport package and the vaporiser when the filling head is in the clamped position against the sealing surface of the conduits leading to the opening.

Anaesthetic agents that are used for anaesthetizing a patient and administered in a stream of inhalation gas are called inhalation anaesthetics. They include for example halothane, enflurane and isoflurane.

Anaesthetic agents are delivered to the place of use in the liquid state. They are transformed to the gaseous form required for administering in an anaesthetic vaporiser specific to each anaesthetic agent. The liquid is transferred from the transport package to the vaporiser by means of a special filling device. The structure of these filling devices ensures that only the transport package of a liquid intended for a given vaporiser can be connected to that vaporiser.

In prior art arrangements the filling device is attached to a bottle acting as the transport package for example by screwing it onto a thread. The filling head to be attached to the vaporiser is in such arrangements a cubical part with two ports situated on one side, one of the ports being intended for the flow of liquid and the other for the flow of a substitute gas. The filling head is positioned in an opening provided in the vaporiser for that purpose. In a place corresponding to the position of the ports of the filling head, the opening comprises ports leading through charging valves to a liquid container in the vaporiser. The filling head is clamped in the opening in such a way that a seal provided in the junction of the ports seals the flow conduits.

When the filling head is attached to the port and the charging valves are open, the liquid container of the vaporiser and the bottle acting as the transport package form via the filling device a closed volume where liquid flows through one of the flow conduits of the filling device towards the container situated at a lower level. In the other conduit the gas flow replacing the liquid flow travels towards the container situated at a higher level. The vaporiser and the transport package have inflexible structures and therefore the flow of the substitute gas is necessary. The vaporiser is filled by lifting the transport package above the liquid container of the vaporiser, and it is correspondingly emptied for example by lowering the transport package below the liquid container of the vaporiser.

It is essential for example in filling that the filling head is clamped to the opening of the vaporiser whenever the charging valves are open. Otherwise the liquid in the vaporiser flows out via the charging valves and the open ports, causing thus pollution of the surrounding air. In conventional vaporisers, the filling device is clamped to the opening of the vaporiser by means of a special clamping screw. After the clamping, the charging valves are opened by means of a separate actuator. When the vaporiser is to be filled or emptied, the filling device must first be clamped in position and then the valves have to be opened separately. When the filling is to be terminated, the valves must be closed first and the filling device is detached last. With respect to its use, the interface is complicated and susceptible to errors.

Different types of mechanical structures have been built to improve the conventional filling device. These structures prevent the opening of a charging valve if the filling device is not clamped in position and vice versa the unlocking of the filling device if the charging valve is not closed. An example of such an arrangement is disclosed in European Patent Application 455,433 A1. In this arrangement the filling device is clamped by means of friction. However, since the filling device has a cubical form and even surfaces it may glide out of the opening, and if the charging valves are open the liquid can thereafter flow out of the container. Another drawback is the complicated mechanical structure.

In order to eliminate the drawbacks of the above-described device, an apparatus where a charging valve is closed automatically when the filling device is removed from the opening has been developed. Finnish Patent Application 923,196 describes this arrangement, which also provides a simplified mechanical structure achieved by eliminating the need to mechanically connect the clamping of the filling device and the charging valves. The drawbacks include that the arrangement requires a means indicating that the filling device is in position, and that the mechanical realization utilizes a spring the load of which acts on the filling device resisting its installation.

Furthermore, the aforementioned arrangements have not managed to eliminate an essential drawback from the interface, i.e. that the filling device is clamped and the charging valves are opened by means of different actuators.

German Offenlegungsschrift 4,106,756 discloses an arrangement where, on the one hand, a charging valve can only remain open when the filling device is in position and, on the other hand, the interface only comprises one actuator. The charging valves are placed in the apparatus in the gripping surface of the filling device in such a way that the valves open automatically when pressed by the filling device that is being clamped in position. The pressing takes place by means of special sliding spring-loaded intermediary sleeves. At the end close to the filling device the sleeves comprise a seal which seals the joint between the filling device and the vaporiser. The sealing takes places in the beginning of the clamping. When the filling device is still clamped after the joint is sealed, pegs attached to the sleeves press against spring-loaded balls acting as valves and open them. Correspondingly, when the filling is ended and the clamping of the filling device is released, the valves are first closed by the action of the aforementioned springs and the sealing surface between the vaporiser and the filling device is opened only after this. The structure is mechanically seemingly simple and easy to use, since the entire operation requires only one actuator.

However, the drawback of the above-described arrangement is that the flow conduits are very narrow. The positioning and the measures of the ports of the filling device are standardized. The distance between the centres of the ports is 6.25 mm. The diameters of the vaporiser ports are 3.2 and 4.8 mm. The space between the ports is thus 2.25 mm. Constructing the opening sleeves and their seals in this space requires very intricate work. Making the ports smaller than the standard in turn throttles the flows and thus increases the filling time. This significantly diminishes the usefulness of the filling mechanism of the vaporiser.

The problems of the above-described filling systems include an unclear interface that is difficult to user mechanical complexity and a low filling rate.

The purpose of the invention is to provide an arrangement by means of which the prior art drawbacks can be eliminated. This has been achieved with the arrangement according to the invention that is characterized in that the arrangement comprises a hydraulic container that contains liquid and arranged thereto a first piston means used to control the pressure of the liquid in the hydraulic container, a second piston means connected to the fastening means of the filling head, said second piston means, under the control of the pressure in the hydraulic container, either clamping the filling head against the sealing surface of the conduits leading to the vaporiser opening or releasing the filling head from the clamping, a third piston means connected to one or several valve means one of which controls the flow of the anaesthetic agent, said third piston means being controlled by the pressure in the hydraulic container to either open or close said one or several valve means.

The primary advantage of the arrangement according to the invention is that the interface is very clear and easy to use. The arrangement according to the invention is also simple, and it is thus economical to carry out and reliable to use. Another advantage is that the arrangement enables the manufacture of such flow conduits of the vaporiser that are as wide as possible, providing thus a high filling rate.

Figure 2:
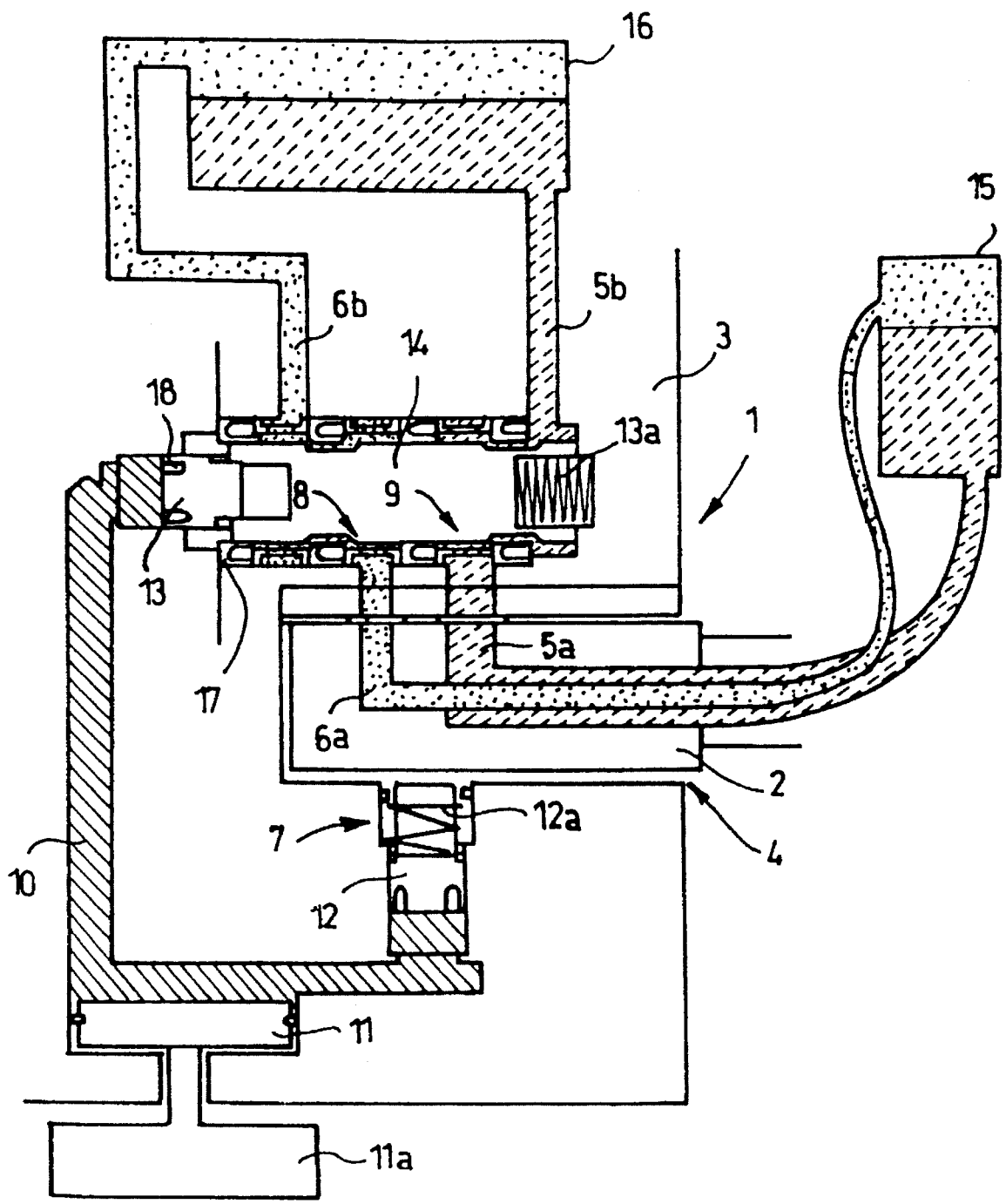
Figure 3:
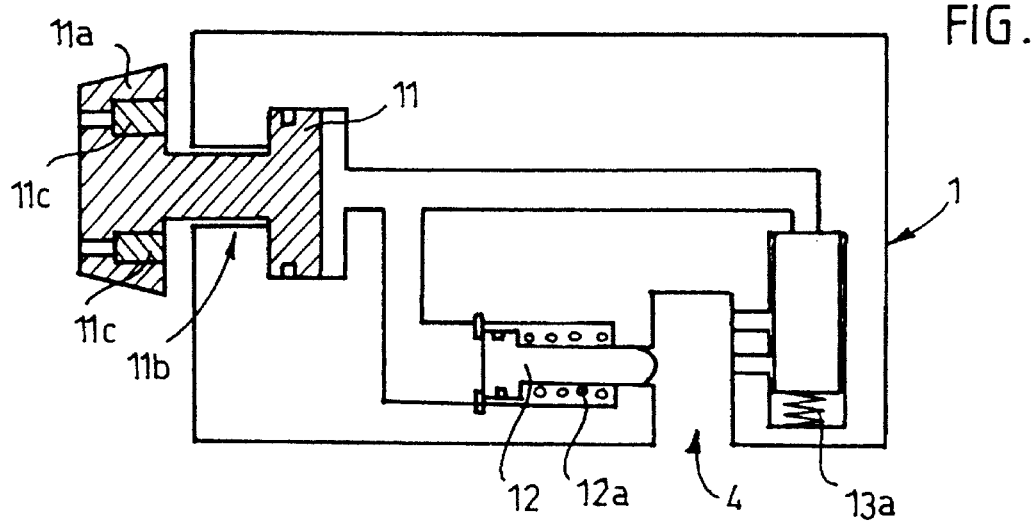
Figure 4:
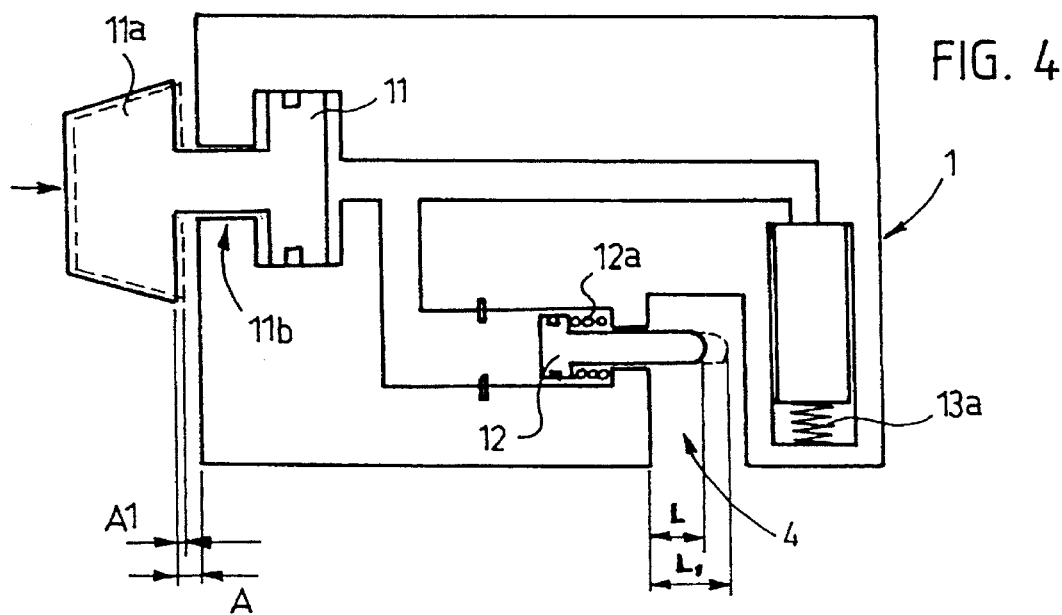
Figure 5:
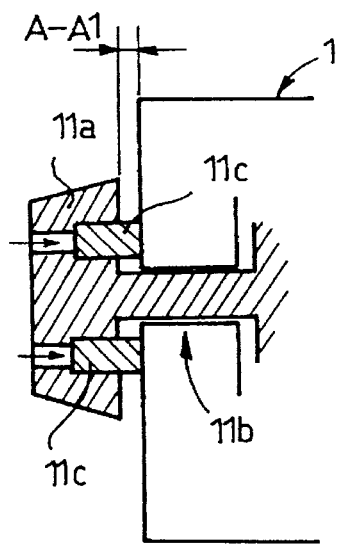

In the following, the invention will be described in greater detail by means of a preferred embodiment shown in the accompanying drawing, in which FIG. 1 is a schematic view of the arrangement according to the invention in a situation where the filling head is not clamped in position in the opening of the vaporiser, FIG. 2 is a schematic view of the arrangement of FIG. 1 in a situation where the filling head is clamped in position in the opening of The vaporiser, and FIGS. 3 to 5 show a preferred embodiment of a detail of the arrangement according to FIGS. 1 and 2.

FIGS. 1 and 2 show the arrangement according to the invention. Reference numeral 1 generally denotes a filling device. The filling device 1 comprises a filling head 2, which can be positioned in an opening 4 provided in a vaporiser 3. The filling device 1 and the vaporiser 3 are provided with conduits 5a, 5b and 6a, 6b intended to take an anaesthetic agent from its transport package to a liquid container in the vaporiser and to take a substitute gas from the liquid container of the vaporiser to the transport package. For the sake of clarity, FIG. 1 does not show the transport package for the anaesthetic agent or the liquid container of the vaporiser in greater detail. They represent fully conventional technology to those skilled in the art, wherefore they will not be described in greater detail in this connection.

The arrangement further comprises a clamping means 7 for clamping the filling head against the wall of the opening 4 of the vaporiser 3. Reference numerals 8 and 9 generally denote valve means that are arranged to open only when the filling head 2 is clamped against the wall of the vaporiser opening 4, thus allowing the anaesthetic agent to flow to the liquid container of the vaporiser and the substitute gas to flow to the transport container for the anaesthetic agent only when the filling head 2 is clamped against the wall of the opening 4.

According to an essential idea of the invention, the arrangement comprises a hydraulic container 10 containing arranged thereto a first piston means 11 for regulating the pressure of the hydraulic container 10, a second piston means 12 attached to the clamping means 7 of the filling head, and a third piston means 13 connected to the valve means 8, 9 that control the flow of the anaesthetic agent and the substitute gas. When the pressure of the hydraulic container 10 is increased, the second piston means 12 is arranged to clamp the filling head 2 against the wall of the vaporiser opening 4 before the third piston means 13 begins to open, as a result of the increasing pressure in the hydraulic container, the valve means 8, 9 to allow the flow of the anaesthetic agent and the substitute gas, and correspondingly when the pressure of the hydraulic container 10 is reduced, the third piston means 13 is arranged to close the valve means 8, 9 before the second piston means 12 begins to release the filling head 2 from its clamped position against the wall of the vaporiser opening 4. It must be noted that the third piston means can also be arranged to act only on the valve means 9 of the liquid conduit. It is thus also possible to provide the arrangement with a fourth piston means which acts on the valve means 8 of the gas conduit, or then the valve means of the gas conduit can be controlled in some other suitable manner.

FIG. 1 shows a situation where the filling head 2 is placed in the opening 4 provided in the vaporiser, but the filling head is not yet clamped against the wall of the opening 4. FIG. 2 shows a situation where the filling head 2 is clamped against the wall of the opening 4.

The second and third piston means 12, 13 can preferably be formed as spring-loaded means so that the spring 12a of the second piston means 12 is arranged to produce a smaller power than the spring 13a of the third piston means 13. This selection of the springs advantageously provides the aforementioned clamping of the filling head and the opening of the valve means, and correspondingly the closing of the valve means and the release of the filling head clamping in the right order. The operation of the arrangement is described in greater detail below.

As it is stated above, the arrangement according to the invention is based on a hydraulic container 10 that contains liquid and comprises attached thereto three separate hydraulic pistons, i.e. piston means 11, 12, 13. One 11 of the pistons is attached to an actuator 11a by means of which the first piston means 11 can be moved and the pressure of the container 10 can thus be regulated. The actuator 11a is described in greater detail below. In the example of the figures, the second piston means 12 is connected to a spring-return clamp of the filling head 2. The third piston means 13 is attached to a spring-return charging valve 14, which comprises the aforementioned valve means 8, 9. The spring 12a of the clamping piston is made lighter than the spring 13a of the valve piston. Therefore, when the pressure of the hydraulic system is increased by means of the actuator 11a, the clamping piston 12 clamps the filling head 2 against the wall of the opening 4 before the charging valve, i.e. the valve means 8, 9, opens. However, a spring might not be necessary in the clamping piston if the kinetic frictions of the pistons are small enough to return the clamping piston by means of hydraulic suction. The charging valve 14, i.e. the valve means 8, 9, opens only when the movement of the clamping piston stops as it meets the filling head 2 fixed in position in the opening 4 of the vaporiser. The power difference of the springs also causes the automatic closing of the charging valve 14 if the filling head 2 is removed when the valve means 8, 9 are open and the clamping piston can freely enter deeper into the opening 4. Thirdly, the charging valve 14 is not opened at all if the filling head 2 is not in position in the opening 4 of the vaporiser when the pressure of the hydraulic system is increased by means of the actuator 11a as the clamping piston 12 freely enters the opening 4 of the filling device.

In order to produce the aforementioned functions, the volume changes of the hydraulic fluid container 10 required by each piston must be taken into consideration in designing the pistons and the extent of their travels. The change in volume between the extremes of travel, brought about by the clamping piston of the filling head 2, i.e. the second piston means 12, is at least as great as the greatest change produced by the pressure-control piston, i.e. the first piston means 11. This is due to the fact that if the filling head 2 is not in place when the pressure-control piston 11 is operated by means of the actuator 11a, the entire change in volume must be directed at the clamping piston 12 in order to keep the piston of the charging valve, i.e. the third piston means 13, and correspondingly the charging valve 14 closed. The change in volume produced by the piston 13 of the charging valve should in turn be smaller than the volume change which is produced by the pressure-control piston 11 and from which the greatest volume change of the clamping piston 12 required to clamp the filling head 2 in place is subtracted. This is due to the fact that the available change of volume can both clamp the filling head 2 and also open the charging valve 14. The change of volume produced by the pressure-control piston 11 is determined by the aforementioned volume changes.

FIG. 1 shows the original situation, i.e. the filling head 2 is placed in the opening 4 provided in the vaporiser. When the pressure of the hydraulic container 10 is increased by means of the actuator 11a and the first piston means 11, the second piston means 12 begins to move upwards in the situation shown in the figures and forces the filling head 2 against the opening wall, i.e. presses it to the position shown in FIG. 2. When the filling head 2 is clamped in the position of FIG. 2 and the pressure is still increased, the third piston means 13 begins to move to the right in the situation shown in the figures and to simultaneously move the charging valve 14 to the right, whereupon the valve means 8, 9 open and allow the anaesthetic agent and the substitute gas to flow in the above-described manner from the transport package 15 to the liquid container 16 of the vaporiser and from the liquid container 16 to the transport package 15, respectively.

When the filling head 2 is removed from the opening, the pressure of the hydraulic container 10 is decreased, whereupon the third piston means 13 first returns to its original position simultaneously closing the valve means 8, 9 and only then the second piston means returns to its original position and releases the filling head 2 from its clamped position against the wall of the opening 4.

A preferred embodiment of the valves for the flow of liquid and substitute gas, i.e. the valve means 8, 9, comprises placing the valves in the elongated charging valve 14 in succession on the same axis for example parallel to the opening 4 of the filling head in the vaporiser in the immediate vicinity of the flow conduits. The volume of the space between the closing point of the valve and the filling head 2 is thus as small as possible. The smaller the volume the less there is liquid in the liquid conduit after the valve is closed. This is essential since any liquid remaining in this space would unnecessarily pollute the surrounding air.

It is significant in the order of opening of the valve means that the valve means 8 of the gas conduit does not open before the valve means 9 of the liquid conduit. If this happened, it might lead to the anaesthetic liquid clogging the gas conduit, thus preventing the filling. If the valve means 9 of the liquid conduit opens first, the liquid flows this way towards the liquid container 16 of the vaporiser forming, by means of a liquid column, overpressure in the vaporiser and a negative pressure in the gas conduit. The pressure difference starts a strong liquid flow as soon as the valve means 8 of the gas conduit opens.

The space between the hydraulic liquid container 10 and the gas conduit of the charging valve 14 comprises preferably both the seal 18 of the piston and also the end seal 17 of the valve. The double seal prevents the mixing of the hydraulic liquid and the anaesthetic liquid if the seal breaks down. It is possible to advantageously place a vent hole in the space between the seals 17, 18, through which vent hole the flow bursts out without getting mixed in case of a possible leaking of the seal.

A preferred embodiment of the actuator 11a of the first piston means 11 is described in FIGS. 3 to 5. The essential idea of the embodiment is that the operation of the actuator 11a to move the piston means 11 and the calibration of the actuator take place by means of a mechanism 11b utilizing a principle of rotation, i.e. the piston means 11 can be moved by rotating a driving knob placed in the device. The calibration of the actuator may take place in the following manner. FIG. 3 shows schematically the original situation. The calibration is performed by rotating the actuator 11a clockwise until the second piston means 12 stops. The second piston means has thus travelled the distance L1. This situation is shown in FIG. 4 with broken lines. The actuator 11a is then rotated anticlockwise for example one turn, whereupon the second piston means moves to position L. One anticlockwise turn of the actuator 11a corresponds to the movement A1 denoted in FIG. 4. It must be noted that when the second piston means 12 is in position L, the filling head 2 cannot be inserted into the opening 4. In the situation shown in FIGS. 3 to 5, the calibration is locked by restricting the movement of the actuator 11a to the right to the distance from A to A1, as described in FIG. 5. The movement may be restricted for example by moving the corresponding parts 11c by means of a suitable mechanism, for instance a screw function.

The above-described embodiment is not intended to restrict the invention in any way, but the invention may be modified quite freely within the scope of the claims. It is therefore clear that the arrangement according to the invention or its details do not necessarily have to be identical to those shown in the figures, but other solutions are also possible. For example the seals can be selected freely according to a given situation.

We claim:

1. An arrangement for filling an anaesthetic vaporiser, the arrangement comprising a filling device to be connected to a transport package for an anaesthetic agent, the filling head of the device being attachable to an opening in the vaporiser, whereupon the filling device and the vaporiser are provided with conduits for transferring the anaesthetic agent between the transport package and the vaporiser and for transferring the substitute gas in the opposite direction, the arrangement comprising a fastening means for clamping the filling head against the sealing surface of conduits leading to the opening in the vaporiser, and one or several valve means arranged to open when the filling head is in the clamped position against the sealing surface of the conduits leading to the vaporiser opening and thus arranged to allow the flow of The anaesthetic agent between the vaporiser and the transport package and the flow of the substitute gas in the opposite direction compared to the anaesthetic agent between the transport package and the vaporiser when the filling head is in the clamped position against the sealing surface of the conduits leading to the opening, the arrangement further comprising a hydraulic container that contains liquid and arranged thereto a first piston means used to control the pressure of the liquid in the hydraulic container, a second piston means connected to the fastening means of the filling head, said second piston means, under the control of the pressure in the hydraulic container, either clamping the filling head against the sealing surface of the conduits leading to the vaporiser opening or releasing the filling head from the clamping, a third piston means connected to one or several valve means one of which controls the flow of the anaesthetic agent, said third piston means being controlled by the pressure in the hydraulic container to either open or close said one or several valve means.

2. An arrangement according to claim 1, wherein the second piston means is arranged to clamp the filling head against the wall of the vaporiser opening when the pressure of the hydraulic container is increased, and correspondingly the second piston means begins to release the filling head from its clamped position against the wall of the vaporiser opening when the pressure of the hydraulic container is decreased.

3. An arrangement according to claim 1, wherein as a result of the pressure increase in the hydraulic container, the third piston means opens the valve means in order to allow the flow of the anaesthetic agent and the substitute gas, and correspondingly when the pressure in the hydraulic container is decreased, the third piston means is arranged to close the valve means to stop the flow of the anaesthetic agent and the substitute gas.

4. An arrangement according to claim 1, wherein the second and third piston means are spring-loaded means, and that the spring of the second piston means is arranged to produce a smaller power than the spring of the third piston means.

5. An arrangement according to claim 1, wherein the change of volume produced by the second piston means between the extremes of movement is at least as great as the greatest possible volume change produced by the first piston means.

6. An arrangement according to claim 1, wherein the volume change required to move the third piston means between the extreme positions is smaller than the volume change which is produced by the first piston means and from which the greatest volume change produced by the second piston means required to clamp the filling head is subtracted.

7. An arrangement according to claim 1, wherein the valve means regulating the flow of the anaesthetic agent is arranged to open before the valve means regulating the flow of the substitute gas.

8. An arrangement according to claim 1, wherein the operation of the actuator of the first piston means to move the piston means, as well as the calibration of the actuator are arranged to take place by means of a mechanism utilizing a principle of rotation.

9. An arrangement according to claim 1, wherein the third piston means is connected to two valve means one of which controls the flow of the anaesthetic agent, and the other the flow of the substitute gas.

10. An arrangement according to claim 9, wherein the second piston means is arranged to clamp the filling head against the wall of the vaporiser opening when the pressure of the hydraulic container is increased, and correspondingly the second piston mans begins to release the filling head from its clamped position against the wall of the vaporiser opening when the pressure of the hydraulic container is decreased.

11. An arrangement according to claim 9, wherein as a result of the pressure increased in the hydraulic container, the third piston means opens the valve means in order to allow the flow of the anaesthetic agent and the substitute gas, and correspondingly when the pressure in the hydraulic container is decreased, the third piston means is arranged to close the valve means to stop the flow of the anaesthetic agent and the substitute gas.

12. An arrangement according to claim 1, wherein the second piston means is arranged to clamp the filling head against the wall of the vaporiser opening when the pressure in the hydraulic container is increased before the third piston means opens the valve means, as a result of the pressure increase of the hydraulic container, to allow the flow of the anaesthetic agent and the substitute gas.

13. An arrangement according to claim 12, wherein the third piston means is arranged to close the valve means to stop the flow of the anaesthetic agent and the substitute gas when the pressure of the hydraulic container is decreased, before the second piston means begins to release the filling head from its clamped position against the wall of the vaporiser opening.

14. An arrangement according to claim 1, wherein the valve means are placed in the elongated charging valve axially in succession.

15. An arrangement according to claim 14, wherein two seals are placed between the liquid space of the hydraulic container and the gas conduit of the charging valve.

16. An arrangement according to claim 14, wherein the valve means are placed in the elongated charging valve axially in succession, parallel to the opening of the filling head provided in the vaporiser.

17. An arrangement according to claim 16, wherein two seals are placed between the liquid space of the hydraulic container and the gas conduit of the charging valve.

* * * * *